US007910733B2

(12) United States Patent
Tian et al.

(10) Patent No.: US 7,910,733 B2
(45) Date of Patent: Mar. 22, 2011

(54) IMAGE-FORMING MATERIAL

(75) Inventors: Minquan Tian, Ashigarakami-gun (JP); Yuka Ito, Ashigarakami-gun (JP); Shinji Hasegawa, Ashigarakami-gun (JP); Kazuhiko Hirokawa, Ashigarakami-gun (JP); Miho Watanabe, Ashigarakami-gun (JP); Makoto Furuki, Ashigarakami-gun (JP); Takashi Matsubara, Ashigarakami-gun (JP); Kazunori Anazawa, Ashigarakami-gun (JP); Tomoko Miyahara, Ashigarakami-gun (JP); Suguru Nakaso, Ashigarakami-gun (JP)

(73) Assignee: Fuji Xerox Co., Ltd., Tokyo (JP)

( * ) Notice: Subject to any disclaimer, the term of this patent is extended or adjusted under 35 U.S.C. 154(b) by 207 days.

(21) Appl. No.: 12/238,488

(22) Filed: Sep. 26, 2008

(65) Prior Publication Data

US 2009/0227793 A1 Sep. 10, 2009

(30) Foreign Application Priority Data

Mar. 5, 2008 (JP) ................................ 2008-055291

(51) Int. Cl.
*C07D 487/00* (2006.01)
*C07D 239/70* (2006.01)

(52) U.S. Cl. ...................................................... 544/249

(58) Field of Classification Search .................. 544/249
See application file for complete search history.

(56) References Cited

U.S. PATENT DOCUMENTS

| | | | | |
|---|---|---|---|---|
| 5,380,635 | A | 1/1995 | Gomez et al. | |
| 5,935,755 | A | 8/1999 | Kazmaier et al. | |
| 6,541,100 | B1 | 4/2003 | Williams et al. | |
| 2010/0071592 | A1* | 3/2010 | Tian et al. | 106/31.97 |

FOREIGN PATENT DOCUMENTS

| | | | |
|---|---|---|---|
| JP | 09-090547 | A | 4/1997 |
| JP | 09-119867 | A | 5/1997 |
| JP | 09-509503 | A | 9/1997 |
| JP | 10-036695 | A | 2/1998 |
| JP | 10-036695 | * | 10/1998 |
| JP | 2000-159776 | A | 6/2000 |
| JP | 2000-162431 | A | 6/2000 |
| JP | 2000-207512 | A | 7/2000 |
| JP | 2001-005141 | A | 1/2001 |
| JP | 2001-294785 | A | 10/2001 |
| JP | 2002-278023 | A | 9/2002 |
| WO | 95/23357 | A1 | 8/1995 |

OTHER PUBLICATIONS

Japanese Office Action dated May 25, 2010 in Japanese application No. 2008-055291.

* cited by examiner

*Primary Examiner* — James O Wilson
*Assistant Examiner* — Erich A Leeser
(74) *Attorney, Agent, or Firm* — Sughrue Mion, PLLC

(57) ABSTRACT

The image-forming material includes a perimidine-based squarylium dye represented by the following formula (I):

(I)

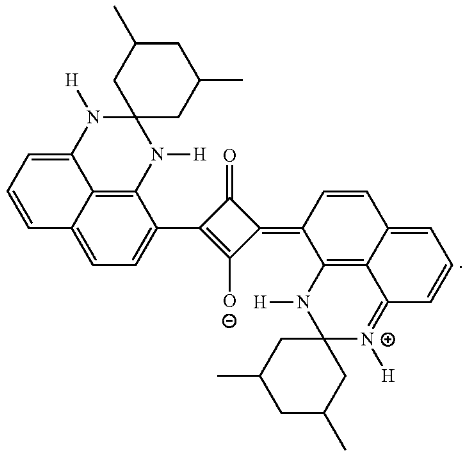

6 Claims, 8 Drawing Sheets

IMAGE-FORMING MATERIAL

CROSS-REFERENCE TO RELATED APPLICATIONS

This application is based on and claims priority under 35 U.S.C. 119 from Japanese Patent Application No. 2008-055291 filed Mar. 5, 2008.

BACKGROUND

1. Technical Field

The present invention relates to an image-forming material.

2. Related Art

In recent years, attention has been given to the technology for recording invisible information, which has no viewability under normal visual conditions, in documents or the like. This technology is useful in security management, embedding of Internet information and voices, and so on, and can enhance the added values of documents and the like.

As one example of a method of recording invisible information, there is a method of utilizing an image-forming material capable of absorbing rays in the near-infrared region of 750 nm to 1,000 nm which are invisible by human eyes but detectable with silicon-based photoreceptors (e.g., CCD).

SUMMARY

According to an aspect of the invention, there is provided an image-forming material, comprising a perimidine-based squarylium dye represented by the following formula (I):

(I)

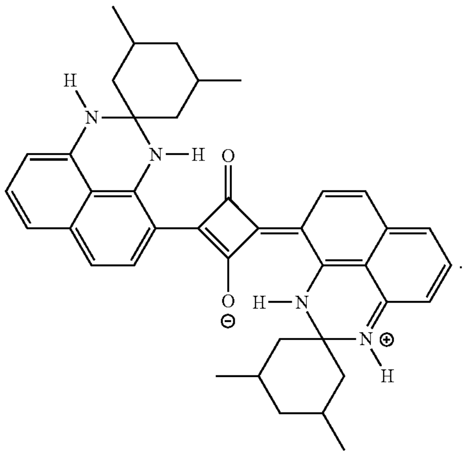

BRIEF DESCRIPTION OF THE DRAWINGS

Exemplary embodiments of the present invention will be described in detail based on the following figures, wherein.

DETAILED DESCRIPTION

Figure 1:
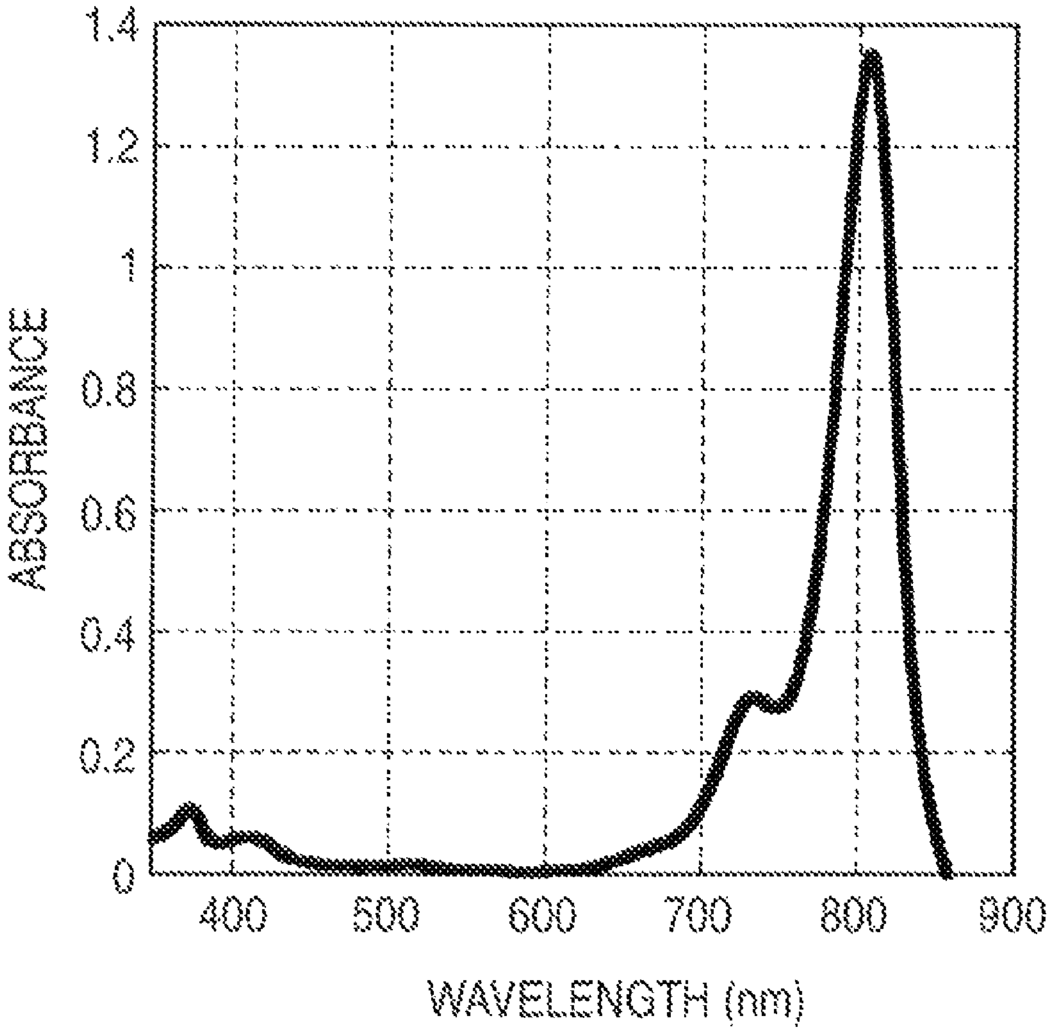
FIG. 1 is a graph showing the visible and near-infrared absorption spectrum of the perimidine-based squarylium dye of formula (I) produced in Example 1.

The foregoing description of the embodiments of the present invention has been provided for the purposes of illustration and description. It is not intended to be exhaustive or to limit the invention to the precise forms disclosed. Obviously, many modifications and variations will be apparent to practitioners skilled in the art. The embodiments were chosen and described in order to best explain the principles of the invention and its practical applications, thereby enabling others skilled in the art to understand the invention for various embodiments and with the various modifications as are suited to the particular use contemplated. It is intended that the scope of the invention be defined by the following claims and their equivalents.

Exemplary embodiments of the invention are illustrated below in detail.

The image-forming material according to the exemplary embodiment of the invention contains the perimidine-based squarylium dye represented by the following formula (I).

(I)

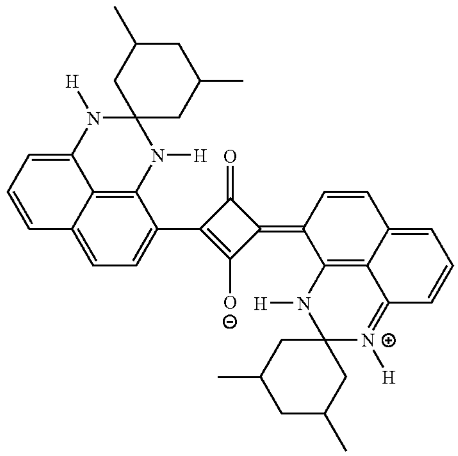

The perimidine-based squarylium dye represented by the formula (I) may be produced in accordance with the following reaction scheme for example.

(A-1)

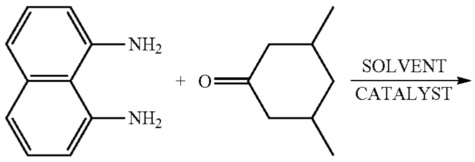

-continued

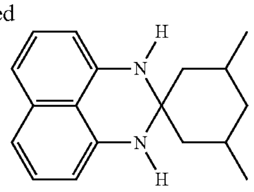

(a)

(A-2)

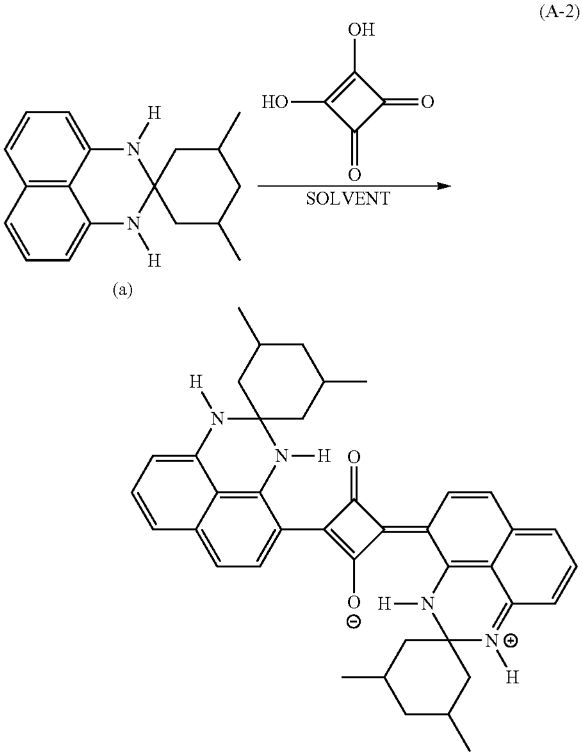

(a)

(I)

More specifically, the perimidine intermediate (a) may be produced by reaction between 1,8-diaminonaphthalene and 3,5-dimethylcyclohexanone in the presence of a catalyst in a solvent under a condition of azeotropic reflux (process step (A-1)). Examples of such a catalyst used in the process step (A-1) include p-toluenesulfonic acid monohydrate, benzenesulfonic acid monohydrate, 4-chlorobenzenesulfonic acid hydrate, pyridine-3-sulfonic acid, ethane sulfonic acid, sulfuric acid, nitric acid, and acetic acid. Examples of such a solvent used in the process step (A-1) include alcohol compounds and aromatic hydrocarbons. The perimidine intermediate (a) may be purified by high-performance column chromatography or recrystallization.

Next, the perimidine-based squarylium dye of the formula (I) may be produced by reaction between the perimidine intermediate (a) and 3,4-dihydroxycyclobut-3-ene-1,2-dione (referred to as squaric acid or quadratic acid too) in a solvent under a condition of azeotropic reflux (process step (A-2)). The process step (A-2) may be performed in an atmosphere of nitrogen gas.

Examples of such a solvent usable in the process step (A-2) include alcohol compounds such as 1-propanol, 1-butanol and 1-pentanol, aromatic hydrocarbons such as benzene, toluene, xylene and monochlorobenzene, ethers such as tetrahydrofuran and dioxane, halogenated hydrocarbons such as chloroform, dichloroethane, trichloroethane and dichloropropane, and amides such as N,N-dimethylformamide and N,N-dimethylacetamide. Herein, alcohol compounds may be used alone, but other solvents such as aromatic hydrocarbons, ethers, halogenated hydrocarbons or amides are preferably used in combination with alcohol-type solvents. Examples of such a solvent include 1-propanol, 2-propanol, 1-butanol, 2-butanol, a mixed solvent of 1-propanol and benzene, a mixed solvent of 1-propanol and toluene, a mixed solvent of 1-propanol and N,N-dimethylformamide, a mixed solvent of 2-propanol and benzene, a mixed solvent of 2-propanol and toluene, a mixed solvent of 2-propanol and N,N-dimethylformamide, a mixed solvent of 1-butanol and benzene, a mixed solvent of 1-butanol and toluene, a mixed solvent of 1-butanol and N,N-dimethylformamide, a mixed solvent of 2-butanol and benzene, a mixed solvent of 2-butanol and toluene, and a mixed solvent of 2-butanol and N,N-dimethylformamide. When such a mixed solvent is used, it is preferable that the alcohol-type solvent concentration is adjusted to 1% or about 1% by volume or above, especially a range of 5% or about 5% to 75% or about 75% by volume.

In the process step (A-2), the mole ratio of the perimidine derivative (a) to 3,4-dihydroxycyclobut-3-ene-1,2-dione (number of moles of perimidine derivative (a)/number of moles of 3,4-dihydoxycyclobut-3-ene-1,2-dione) is preferably from 1 or about 1 to 4 or about 4, more preferably from 1.5 or about 1.5 to 3 or about 3. When the mole ratio is smaller than 1, there is a tendency to lower the yield of the perimidine-based squarylium dye represented by the formula (I). When the mole ratio is greater than 4, on the other hand, there is a tendency to worsen utilization efficiency of the perimidine derivative (a) to result in difficulty of isolating and purifying the compound represented by the formula (I).

In addition, when a dehydrator is used in the process step (A-2), the trend is for the reacting time to decrease and the yield of the perimidine-based squarylium dye of the formula (I) to increase. The dehydrator usable herein has no particular restriction so long as it is unreactive to the perimidine intermediate (a) and 3,4-dihydroxycyclobut-3-ene-1,2-dione, but preferred ones thereof include orthoformates, such as trimethyl orthoformate, triethyl orthoformate, tripropyl orthoformate and tributyl orthoformate, and molecular sieve.

The reaction temperature in the process step (A-2) depends on the species of the solvent used, but it is preferable that the temperature of the reacting solution is adjusted to about 60° C. or above, especially to about 75° C. or above. When the solvent used is, e.g., a mixed solvent of 1-butanol and toluene, the temperature of the reacting solution is preferably from 75° C. or about 75° C. to 105° C. or about 105° C.

The reacting time in the process step (A-2) depends on the species of the solvent used and the temperature of the reacting solution. When the reaction is performed using, e.g., a mixed solvent of 1-butanol and toluene as the temperature of the reacting solution is kept at, e.g., a range of 90° C. or about 90° C. to 105° C. or about 105° C., the reacting time is preferably from 2 or about 2 hours to 4 or about 4 hours.

The perimidine-based squarylium dye of the formula (I) produced in the process step (A-2) may be purified by solvent wash, high-performance column chromatography or recrystallization.

In the image-forming material according to the exemplary embodiment of the invention, it is preferable that the perimidine-based squarylium dye represented by the formula (I) is present in a state of particles. The compound represented by the formula (I) has strong intermolecular interaction and particles thereof has high crystallinity, so the image-forming material may have further enhanced infrared color-development capability and light stability by including such particles of the formula (I).

Particles of the perimidine-based squarylium dye represented by the formula (I) may be formed, e.g., as follows: The compound purified after the process step (A-2) is dissolved in tetrahydrofuran, the resulting solution is injected into distilled water, which is stirred and cooled by ice, with a syringe or the like, thereby forming a precipitate, and the precipitate thus formed is filtered off by suction filtration, washed with distilled water and then subjected to vacuum drying. Herein, the particle size of the precipitate thus prepared may be adjusted to fall within a desired range by controlling the concentration of the perimidine-based squarylium dye represented by the formula (I) in the solution, the injection speed of the solution, the quantity or temperature of distilled water used, the stirring speed and so on. The median diameter d50 of particles of the perimidine-based squarylium dye represented by the formula (I) is preferably from 10 or about 10 nm to 300 or about 300 nm, far preferably from 20 or about 20 nm to 200 or about 200 nm. When the median diameter d50 is smaller than 10 nm, the dye molecules in each particle are in a state close to monomolecular dispersion, and the intermolecular interaction becomes weak. So, the light stability of the dye particles tends to decrease. On the other hand, when the median diameter d50 is greater than 300 nm, light scattered from the particle surfaces increases, so the infrared color-development capability tends to decrease.

Although the image-forming material according to the exemplary embodiment of the invention may contain ingredients as recited hereinafter in addition to the perimidine-based squarylium dye of the formula (I), the perimidine-based squarylium dye content is preferably from 0.05% or about 0.05% to 3% or about 3% by weight, far preferably from 0.1% or about 0.1% to 2% or about 2% by weight, based on the total weight of the image-forming material.

The image-forming material according to the exemplary embodiment of the invention has no particular restriction as to its use, but suitable examples of its use include electrophotographic toner, inkjet printer's ink, and ink for letterpress printing, offset printing, flexographic printing, gravure printing or silk-screen printing.

When the image-forming material according to the exemplary embodiment of the invention is electrophotographic toner, it may be used alone as a one-component developer, or may be used in combination with a carrier as a two-component developer. As the carrier, publicly known carriers may be used. As an example of the carrier, a resin-coated carrier having a coating layer of resin on a core material may be given. Into the coating layer of resin, electrically conductive powder or the like may be dispersed.

When the image-forming material according the exemplary embodiment of the invention is electrophotographic toner, it may further contain a binder resin. Examples of such a binder resin usable herein include homo- and copolymers having as constituent monomers styrene compounds such as styrene and chlorostyrene, monoolefins such as ethylene, propylene, butylene and isoprene, vinyl esters such as vinyl acetate, vinyl propionate, vinyl benzoate and vinyl butyrate, α-methylene aliphatic monocarboxylic acid esters such as methyl acrylate, ethyl acrylate, butyl acrylate, dodecyl acrylate, octyl acrylate, phenyl acrylate, methyl methacrylate, ethyl methacrylate, butyl methacrylate and dodecyl methacrylate, vinyl ethers such as vinyl methyl ether, vinyl ethyl ether and vinyl butyl ether, or/and vinyl ketones such as vinyl methyl ketone, vinyl hexyl ketone and vinyl isopropenyl ketone. The representatives of these binder resins include polystyrene, styrene-alkyl acrylate copolymers, styrene-alkyl methacrylate copolymers, styrene-acrylonitrile copolymers, styrene-butadiene copolymers, styrene-maleic anhydride copolymers, polyethylene and polypropylene. In addition, polyester, polyurethane, epoxy resin, silicone resin, polyamide, denatured rosin and paraffin wax may also be used as binder resin.

When the image-forming material according to the exemplary embodiment of the invention is electrophotographic toner, it may further contain an electrification control agent and an anti-offset agent as required. As the electrification control agent, there are two types, an agent used in the case of positive charging and an agent used in the case of negative charging. Examples of such an electrification control agent for use in the case of positive charging include quaternary ammonium compounds, while those for use in the case of negative charging include metal complexes of alkylsalicylic acid and resins having polar groups. Examples of such an anti-offset agent usable therein include low-molecular-weight polyethylene and low-molecular-weight polypropylene.

When the image-forming material according to the exemplary embodiment of the invention is electrophotographic toner, inorganic powdery particles or organic particles may be added to the toner surface as an external additive for the purposes of enhancing flowability and powder keeping quality, controlling frictional electrification, increasing transfer capability and cleaning properties, and so on. Examples of such inorganic powdery particles include heretofore known ones, such as silica, alumina, titania, calcium carbonate, magnesium carbonate, calciumphosphate and cerium oxide. Further, these inorganic powdery particles may be subjected to known surface treatment in response to the intended purpose. Examples of such organic particles which may be added for the foregoing purposes include emulsion polymers having as their respective constituents vinylidene fluoride, methyl methacrylate, a combination of styrene and methyl methacrylate or so on, or soap-free polymers.

When the image-forming material according to the exemplary embodiment of the invention is inkjet printer's ink, it may take the form of water-containing aqueous ink. In addition, the image-forming material according to the exemplary embodiment of the invention may further contain a water-soluble organic solvent for the purposes of preventing the ink from drying and enhancing permeability of the ink. Examples of water usable therein include ion exchange water, ultrafiltered water and deionized water. And examples of such an organic solvent usable therein include polyhydric alcohols such as ethylene glycol, diethylene glycol, polyethylene glycol and glycerin, N-alkylpyrrolidones, esters such as ethyl acetate and amyl acetate, lower alcohols such as methanol, ethanol, propanol and butanol, and glycol ethers such as ethylene oxide or propylene oxide adducts of methanol, butanol or phenol. These organic solvents may be used alone or as mixtures of two or more thereof. The organic solvent used in the ink are chosen as appropriate with consideration given to their hygroscopic properties, their moisture-retaining properties, the solubility of the perimidine-based squarylium dye represented by the formula (I), their permeability properties, the viscosity of the resulting ink, their freezing points and so on. The organic solvent content in the inkjet printer's ink is preferably from 1% or about 1% to 60% or about 60% by weight.

Further, when the image-forming material according to the exemplary embodiment of the invention is inkjet printer's ink, it may contain additives heretofore known as ingredients of the ink in order to satisfy requirements for inkjet printer systems. Examples of such additives include a pH adjuster, a resistivity adjuster, an antioxidant, an antiseptic, a fungicide and a sequestering agent. Examples of such a pH adjuster usable therein include alcoholamines, ammonium salts and metal hydroxides. Examples of such a resistivity adjuster usable therein include organic salts and inorganic salts. And examples of such a sequestering agent usable therein include chelating agents.

Furthermore, when the image-forming material according to the exemplary embodiment of the invention is inkjet printer's ink, it may also contain a water-soluble resin, such as polyvinyl alcohol, polyvinyl pyrrolidone, carboxymethyl cellulose, a styrene-acrylic acid resin or a styrene-maleic acid resin, in an amount not to cause clogging of a jet nozzle, a change in direction of a jet of ink, and so on.

When the image-forming material according to the exemplary embodiment of the invention is ink for letterpress printing, offset printing, flexographic printing, gravure printing or silk-screen printing, it may take the form of oil ink containing a polymer and an organic solvent. Examples of such a polymer generally used herein include natural resins, such as protein, rubber, cellulose, shellac, copal, starch and rosin; thermoplastic resins, such as vinyl resins, acrylic resins, styrene resins, polyolefin resins and novolak-type phenol resins; and thermosetting resins, such as resol-type phenol resins, urea resins, melamine resins, polyurethane resins, epoxy resins and unsaturated polyesters. Examples of such an organic solvent usable therein include the organic solvents recited in the foregoing description of the inkjet printer's ink.

In addition, when the image-forming material according to the exemplary embodiment of the invention is ink for letterpress printing, offset printing, flexographic printing, gravure printing or silk-screen printing, it may further contain additives, such as a plasticizer for enhancing flexibility and strength of the film formed by printing, a solvent for viscosity adjustment and enhancement of drying properties, a drying agent, a viscosity adjuster, a dispersing agent and various kinds of reactants.

Although the perimidine-based squarylium dye represented by the formula (I) has high light stability, it is also possible that the image-forming material according to the exemplary embodiment of the invention further contains a stabilizer for achieving higher light stability in each of the uses. Such a stabilizer is required to receive energy from the organic near-infrared absorbing dye in an excited state, so it is preferable that the stabilizer has an absorption band on the side of longer wavelengths than the absorption band of the near-infrared absorbing dye. In addition, it is also preferable that the stabilizer resists decomposition by singlet oxygen and has high compatibility with the perimidine-based squarylium dye represented by the formula (I). As stabilizers meeting such conditions, organic metal complex compounds may be given. Suitable examples of such stabilizers include compounds represented by the following formula (V).

(V)

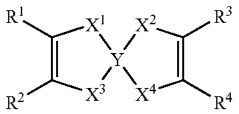

In the formula (V), $R^1$ to $R^4$ may be the same or different, and each represents a substituted or unsubstituted phenyl group. When the phenyl groups represented by $R^1$ to $R^4$ have substituents, examples of such substituents include $NH_2$, OH, $N(C_hH_{2h+1})_2$, $OC_hH_{2h+1}$, $C_hH_{2h-1}$, $C_hH_{2h+1}$, $C_hH_{2h}OH$ and $C_hH_{2h}OC_iH_2$i+l (wherein h is an integer of 1 to 18 and i is an integer of 1 to 6). And $X^1$ to $X^4$ may be the same or different, and each represents O, S or Se, and Y represents a transition metal, such as Ni, Co, Mn, Pd, Cu or Pt.

Of the compounds represented by the formula (V), the compound represented by the following formula (VI) is especially preferred.

(VI)

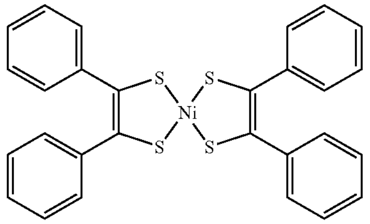

The weight-percentage concentration of such a stabilizer is preferably of the order of 1/10 or about 1/10 to 2 or about 2 times that of the perimidine-based squarylium dye represented by the formula (I).

The perimidine-based squarylium dye represented by the formula (I) has sufficiently low absorbance in the visible wavelength region of 400 nm to 750 nm and sufficiently high absorbance in the near-infrared wavelength region of 750 nm to 1,000 nm. Besides, the perimidine-based squarylium dye represented by the formula (I) has high light stability. Accordingly, the image-forming materials containing such a perimidine-based squarylium dye in accordance with exemplary embodiments of the invention may attain compatibility between invisibility of the information and readability-of the invisible information, and may further ensure long-term stability in invisible information-bearing recording media.

It is preferable that the image-forming material according to the exemplary embodiment of the invention satisfies the conditions given by the following expressions (II) and (III). The satisfaction of the conditions given by expressions (II) and (III) allows compatibility between invisibility of the information and readability of the invisible information irrespective of what color the image-forming material has, and furthermore, may ensure long-term reliability in invisible information-bearing recording media.

$$0 \leqq \Delta E \leqq 16 \quad \text{(II)}$$

$$(100-R) \geqq 75 \quad \text{(III)}$$

In the formula (II), ΔE represents a color difference defined by the following expression (IV) in CIE1976L*a*b* color specification system:

$$\Delta E=\sqrt{(L_1-L_2)^2+(a_1-a_2)^2+(b_1-b_2)^2} \quad \text{(IV)}$$

wherein $L_1$, $a_1$ and $b_1$ respectively represent an L-value, an a-value and a b-value of a recording medium surface before image formation, and $L_2$, $a_2$ and $b_2$ respectively represent an L-value, an a-value and a b-value of an image area at the time of formation of a fixed image in an adhesion amount of 4 $g/m^2$ on the recording medium surface by use of the above-mentioned image-forming material. In the formula (III), R (unit: %) represents a reflectivity that the image area has when an infrared ray with a wavelength of 850 nm strikes thereon.

The foregoing $L_1$, $a_1$, $b_1$, $L_2$, $a_2$ and $b_2$ may be determined by measurements with a reflection spectrodensitometer. The $L_1$, $a_1$, $b_1$, $L_2$, $a_2$ and $b_2$ values in the invention are values measured by using X-Rite 939, made by X-Rite, Inc., as the reflection spectrodensitometer.

The invisible information recorded with the image-forming material according to the exemplary embodiment of the invention may be read simply and sensitively by using a semiconductor laser or a light-emitting diode that can be luminous at any of wavelengths in, e.g., the 750- to 1,000-nm range as a light source for optical readout as well as a general-purpose photoreceptor having high spectral sensitivity to the near-infrared light. As an example of the photoreceptor, a silicon-based photoreceptor (CCD or the like) may be given.

EXAMPLES

The invention will now be illustrated in further detail by reference to Examples and Comparative Examples, but the invention should not be construed as being limited to the following Examples in any way.

Example 1

(Making of Perimidine-Based Squarylium Dye: Two-Step Synthesis)

A mixed solution containing 4.843 g (98%, 30.0 mmol) of 1,8-diaminonaphthalene, 3.886 g (98%, 30.2 mmol) of 3,5-dimethylcyclohexanone, 10 mg (0.053 mmol) of p-toluenesulfonic acid monohydrate and 45 ml of toluene is heated and refluxed for 5 hours with stirring in an atmosphere of nitrogen gas. The water produced during the reaction is removed by azeotropic distillation. After the completion of the reaction, the toluene is distilled away, and the resulting dark brown solid is extracted with acetone, purified by recrystallization from a mixed solvent of acetone and ethanol, and then dried, thereby yielding 7.48 g (yield: 93.6%) of brown solid. Analytical results of $^1$H-NMR spectrum ($CDCl_3$) of the brown solid thus obtained are shown below.

$^1$H-NMR spectrum ($CDCl_3$): δ=7.25, 7.23, 7.22, 7.20, 7.17, 7.15 (m, 4H, $H_{arom}$); 6.54 (d×d, $J_1$=23.05 Hz, $J_2$=7.19 Hz, 2H, $H_{arom}$); 4.62 (br s, 2H, 2×NH); 2.11 (d, J=12.68 Hz, 2H, $CH_2$); 1.75, 1.71, 1.70, 1.69, 1,67, 1.66 (m, 3H, 2×CH, $CH_2$); 1.03 (t, J=12.68 Hz, 2H, $CH_2$); 0.89 (d, J=6.34 Hz, 6H, 2×$CH_3$); 0.63 (d, J=11.71 Hz, 1H, $CH_2$)

Then, a mixed solution containing 4.69 g (17.6 mmol) of the above-described brown solid, 913 mg (8.0 mmol) of 3,4-dihydroxycyclobut-3-ene-1,2-dione, 40 ml of n-butanol and 60 ml of toluene, is heated and refluxed for 3 hours with stirring in an atmosphere of nitrogen gas. The water produced during the reaction is removed by azeotropic distillation. After the completion of the reaction, most of the solvents are distilled away in an atmosphere of nitrogen gas, and 120 ml of hexane is added to the resulting reaction mixture with stirring. The thus formed blackish brown precipitate is collected by suction filtration, washed with hexane, and then dried, thereby yielding a blackish blue solid. This solid is washed successively with ethanol, acetone, 60% aqueous ethanol, ethanol and acetone, thereby giving 4.30 g (yield: 88%) of the desired compound (blackish blue solid).

The dye compound produced is identified by means of its infrared spectrum (KBr pellet method), $^1$H-NMR (DMSO-$d_6$), FD-MS, elemental analyses and spectroscopy such as visible and near-infrared absorption spectral measurement. The identification data are shown below. The visible and near-infrared absorption spectrum is shown in FIG. 1. As a result of identification, the compound produced is ascertained to be the perimidine-based squarylium dye represented by the formula (I).

Infrared Spectrum (KBr pellet method):

$\nu_{max}$=3487, 3429, 3336 (NH), 3053 (=C—H), 2947 ($CH_3$), 2914, 2902 ($CH_2$), 2864 ($CH_3$), 2360, 1618, 1599, 1558, 1541 (C=C ring), 1450, 1421, 1363 ($CH_3$, $CH_2$), 1315, 1223, 1201 (C—N), 1163, 1119 (C—$O^-$), 941, 924, 822, 783, 715 $cm^{-1}$ $^1$H-NMR Spectrum (DMSO-$d_6$):

δ=10.52 (m, 2H, NH); 7.80, 7.78 (d, 2H, $H_{arom}$): 7.35, 7.33 (m, 2H, $H_{arom}$): 7.25 (m, 2H, NH); 6.82, 6.80, 6.78 (m, 4H, $H_{arom}$): 6.74, 6.72, 6.52, 6.50 (m, 2H, $H_{arom}$); 2.17 (m, 4H, $CH_2$); 1.91 (m, 3H, CH, $CH_2$); 1.71 (m, 3H, CH, $CH_2$); 1.15, 1.12 (m, 4H, $CH_2$); 0.92, 0.91 (m, 12H, 4×$CH_3$); 0.66 (m, 2H, $CH_2$)

Mass Spectrum (FD):

m/z=610 ($M^+$, 100%), 611 ($M^+$+1, 47.5%)

Elemental Analysis:

C: 78.6% (Found), 78.66% (Calcd.)
H: 6.96% (Found), 6.93% (Calcd.)
N: 9.02% (Found), 9.17% (Calcd.)
O: 5.42% (Found), 5.24% (Calcd.)

Visible and Near-Infrared Absorption Spectrum (FIG. 1):

$\lambda_{max}$=809 nm (in tetrahydrofuran solution)
$\epsilon_{max}$=1.68×10$^5$ $M^{-1}cm^{-1}$ (in tetrahydrofuran solution)

Example 2

Treatment for Conversion into Pigment and Colorimetric Evaluation

Treatment for converting the perimidine-based squarylium dye produced in Example 1 into pigment and colorimetric evaluations on the pigment were performed as follows.

(Treatment 1 for Fine Particle Formation)

Figure 2:
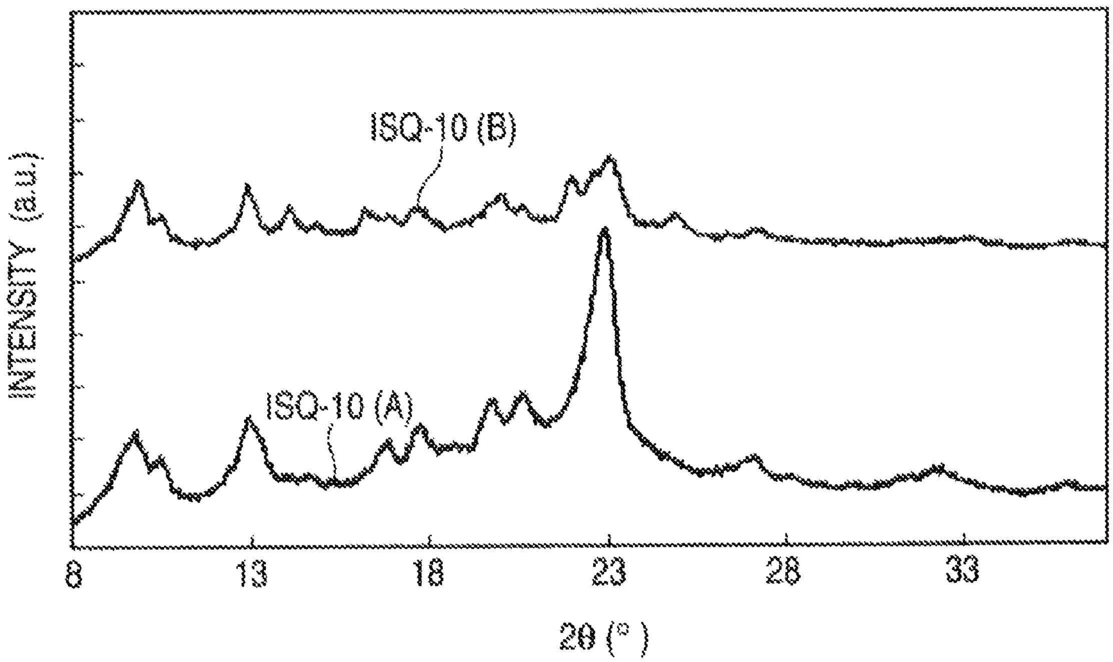
FIG. 2 is a graph showing the powder X-ray diffraction spectra of ISQ-10(A) and ISQ-10(B)
Figure 3:
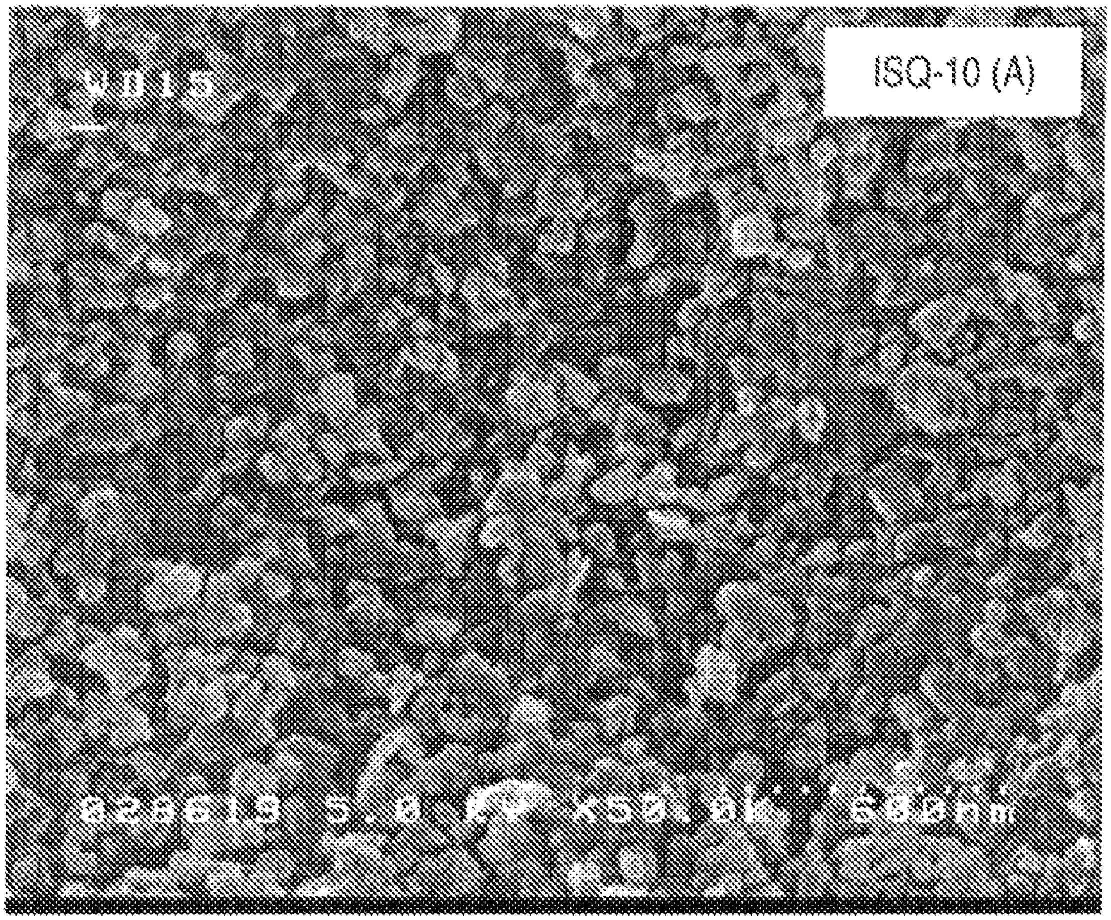
FIG. 3 displays an SEM photograph of ISQ-10(A)

In a ball mill vessel, 50 mg of the perimidine-based squarylium dye produced in Example 1, 1 mL of tetrahydrofuran (THF) and 10 g of zirconia beads measuring 1 mm in diameter are placed, and subjected to 1-hour milling treatment. Then, water is added to the ball mill vessel, and the resulting mixture is passed through a 50-nm filter to collect the perimidine-based squarylium dye formed into fine particles (hereinafter referred to as "ISQ-10(A)"). The particle diameter of ISQ-10 (A) is found to be about 30 nm in terms of median diameter d50. X-ray diffraction measurement of ISQ-10(A) is performed under irradiation with X-ray of λ=1.5405 Å from a Cu target by means of an X-ray diffraction instrument (D8 DISCOVER, made by Bruker AXS K. K.). The powder X-ray diffraction spectrum measured is shown in FIG. 2. In this powder X-ray diffraction spectrum, ISQ-10(A) shows diffraction peaks at least at angles 9.9°, 13.2°, 19.9°, 20.8° and 23.0° corresponding to 2θ±0.20 (θ: Bragg angle) These measurement results of the powder X-ray diffraction reveal that ISQ-10(A) has high crystallinity. In addition, an SEM photograph of ISQ-10(A) is shown in FIG. 3.

(Preparation of Slurry)

Figure 4:
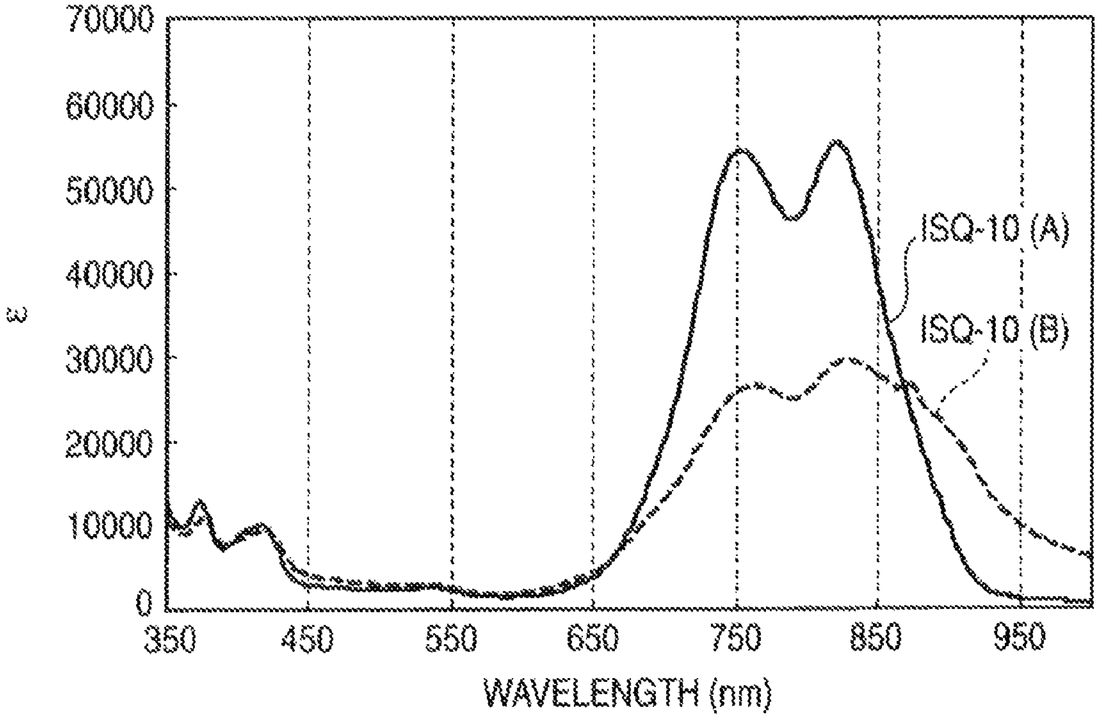
FIG. 4 is a graph showing the visible and near-infrared absorption spectrum of slurry prepared using ISQ-10(A) and that of slurry prepared using ISQ-10(B)

ISQ-10(A) in an amount of 9.2 mg, together with 46 μl of a 12% aqueous solution of Triton X-100 and 5.52 ml of distilled water, is subjected to ultrasonic dispersion (ultrasonic power: 4-5 W, use of a ¼ inch horn, irradiation time of 30 minutes), and thereby formed into slurry. The sample concentration in the slurry is 0.165 wt %. The visible and near-infrared absorption spectrum of the slurry thus prepared is shown in FIG. 4.

(Preparation of Slurry-Coated Paper and Color Performance Evaluation)

Figure 5:
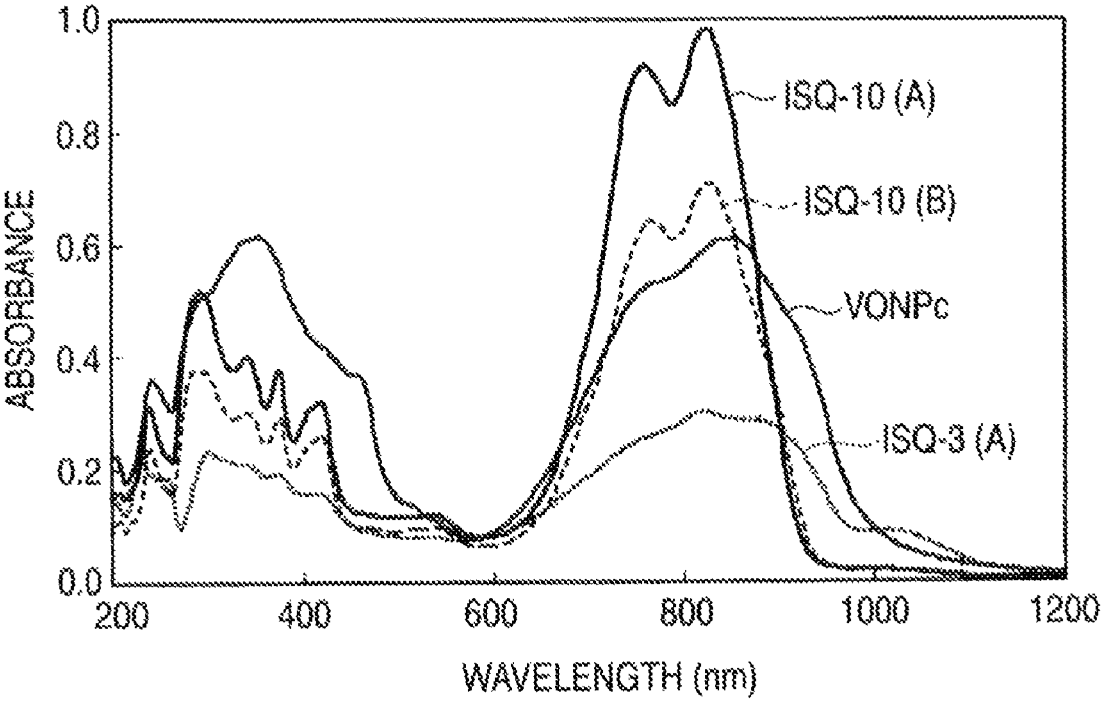
FIG. 5 is a graph showing the absorption spectra of latex patches prepared using ISQ-10(A), ISQ-10(B), VONPc and ISQ-3(A), respectively.

A mixed solution of 40.4 μl of the slurry of ISQ-10(A) (sample concentration: 0.165 wt %), 15 μl of a 40 wt % latex (copolymer of styrene and n-butyl acrylate) and 5 g of distilled water is subjected to dispersion treatment with Ultra- Turrax. Thus, a mixed slurry is prepared. From this mixed slurry, a pseudo-toner dispersion liquid is prepared by addition of PAC as a flocculent. This dispersion liquid is filtered off by a 220-nm filter paper, and the resulting lamination layer on the paper is air-dried, and then subjected to thermocompression bonding (120° C., mode 1). Thus, a latex patch for evaluation (TMA=4.5 g/$m^2$, amount of pigment per unit area PMA=0.045 g/$m^2$ (equivalent of 1 wt %)) is made. The coated paper thus made is used as a sample, and measurements thereon are performed with a spectrophotometer U-4100, made by Hitachi, Ltd. The absorption spectrum of the latex patch is shown in FIG. 5.

In addition, measurements on the pigment formed from ISQ-10(A) are performed with a reflection spectrodensitometer (X-Rite 939, made by X-Rite, Inc.), and thereby ΔE in the formula (II) and R in the formula (III) are determined. Evaluation results of the coated paper sample are shown in Table 1.

(Light Stability Test)

Figure 6:
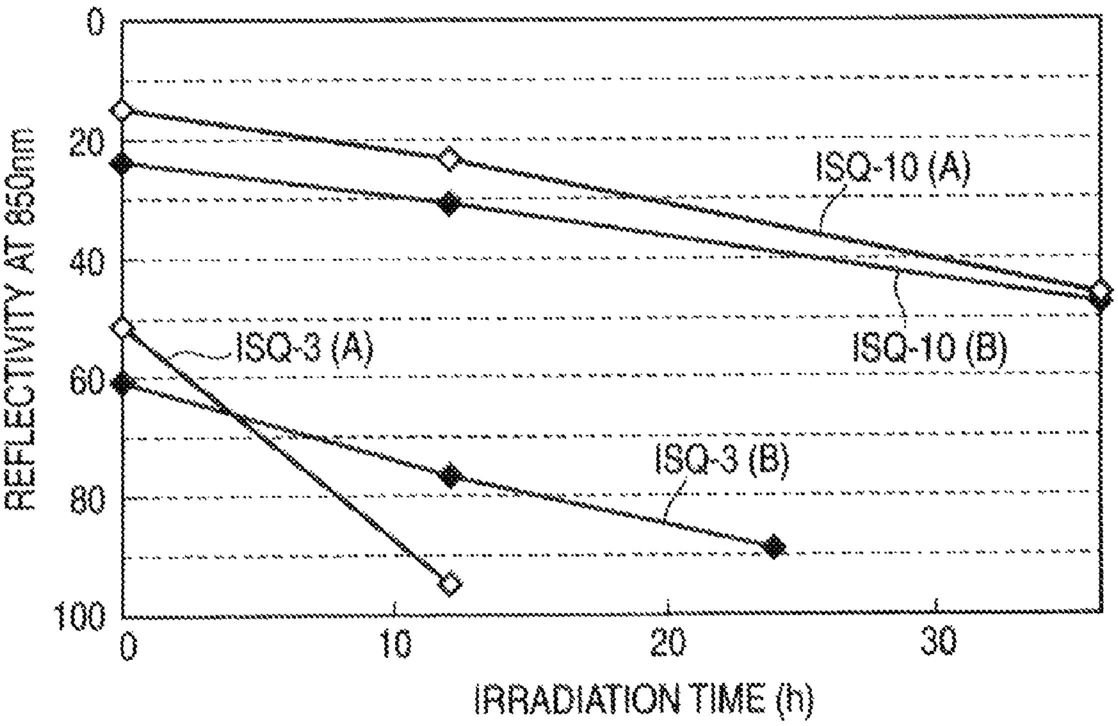
FIG. 6 is a graph showing the reflectivity-to-irradiation time relationships existing in the coated paper samples prepared using ISQ-10(A), ISQ-10(B), ISQ-3(A) and ISQ-3(B), respectively.

The coated paper sample is subjected to 36-hour irradiation with light (light source: xenon lamp, irradiance: 540 W/$m^2$=100 klux, without a UV cut-off filter). During the irradiation, peak absorbance measurements are performed with a spectrophotometer U-4100, made by Hitachi, Ltd. The relationship between the reflectivity of the coated paper sample and irradiation time is shown in FIG. 6.

Additionally, the criteria for evaluations of "readability" and "invisibility" in Table 1 are as follows (which are the same hereinafter).

(Readability)

A: Initial Reflectivity R (%) at 850 nm≦15

B: 15<Initial Reflectivity R (%) at 850 nm ≦30

C: Initial Reflectivity R (%) at 850 nm>30

(Invisibility)

A: 0≦ΔE≦5

B: 5<ΔE≦16

C: ΔE>16

Example 3

Treatment for converting the perimidine-based squarylium dye produced in Example 1 into pigment is performed as follows.

(Treatment 2 for Fine Particle Formation)

Figure 7:
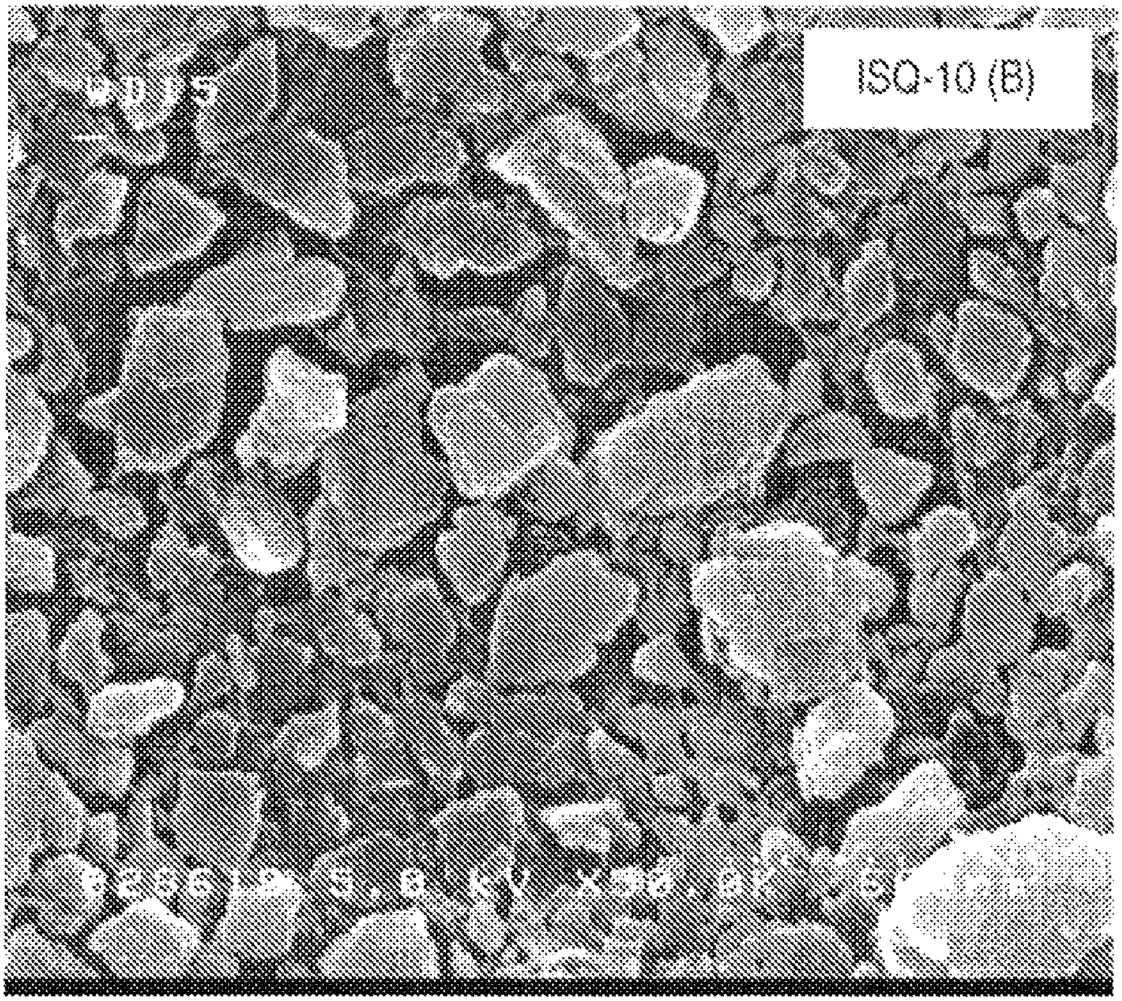
FIG. 7 displays an SEM photograph of ISQ-10(B)

In a ball mill vessel, 100 mg of the perimidine-based squarylium dye produced in Example 1, 1 mL of THF and 10 g of agate beads measuring 1 mm in diameter are placed, and subjected to 8-hour milling treatment. Then, water is added to the ball mill vessel, and the resulting mixture is passed through a 50-nm filter to collect the perimidine-based squarylium dye formed into fine particles (hereinafter referred to as "ISQ-10(B)"). The particle diameter of ISQ-10(B) is found to be about 150 nm in terms of median diameter d50. A powder X-ray diffraction spectrum of ISQ-10(B) measured under irradiation with X-ray of λ=1.5405 Å from a Cu target, as in the case of ISQ-10(A) in Example 2, is shown in FIG. 2. In this powder X-ray diffraction spectrum, ISQ-10(B) shows diffraction peaks at least at angles 9.9°, 13.2°, 19.9°, 20.8° and 23.0° corresponding to 2θ±0.2° (θ: Bragg angle), which proved that ISQ-10(B) has crystallinity. Additionally, when compared to ISQ-10(A), ISQ-10(B) has different peak-intensity ratios and its peak intensities are weak as a whole. Further, an SEM photograph of ISQ-10(B) is shown in FIG. 7. When FIG. 7 is put in contrast with FIG. 3, it is apparent that the shape of ISQ-10(B) is different from that of ISQ-10(A).

A slurry and a slurry-coated paper are prepared using ISQ-10(B) in the same manner as in Example 2, and thereon the color performance evaluations and the light stability test are made. The results obtained are shown in FIG. 4, FIG. 5, FIG. 6 and Table 1, respectively.

Example 4

(Making of Perimidine-Based Squarylium Dye: One-Pot Synthesis)

A mixed solution containing 4.68 g (98%, 29.0 mmol) of 1,8-diaminonaphthalene, 3.74 g (98%, 29.1 mmol) of 3,5-dimethylcyclohexanone, 20 mg (0.11 mmol) of p-toluene-sulfonic acid monohydrate and 45 ml of toluene is heated and refluxed for 2 hours with stirring in an atmosphere of nitrogen gas. The water produced during the reaction is removed by azeotropic distillation. After cooling, to this reaction solution, 1.14 g (10.0 mmol) of 3,4-dihydroxycyclobut-3-ene-1,2-dione, 70 ml of n-butanol and 70 ml of toluene are added. While heating this mixed solution with stirring in an atmosphere of nitrogen gas, dehydration reflux is carried out for 1.5 hours. Thereafter, the reaction solution is cooled for a time, and thereto 376 mg (3.3 mmol) of 3,4-dihydroxycyclobut-3-ene-1,2-dione is further added. Then, the reaction mixture is refluxed for additional 1.5 hours. The water produced during the reaction is removed by azeotropic distillation. After the completion of the reaction, the toluene is distilled away in an atmosphere of nitrogen gas, and the resulting reaction mixture is cooled to room temperature. The precipitate thus formed is filtered off under a reduced pressure, washed with 2-propanol, and then dried. Thus, 7.4 g of blackish blue powder is obtained (yield: 91%). As a result of identification by spectroscopy including visible and near-infrared absorption spectral measurement, the perimidine-based squarylium dye produced in this example has the same structure as the perimidine-based squarylium dye produced in Example 1 and is equal in purity level to the perimidine-based squarylium dye produced in Example 1.

Comparative Example 1

The same colorimetric evaluations as in Example 2 are made on a vanadyl naphthalocyanine dye currently in use (hereinafter referred to as "VONPc"). Results obtained are shown in Table 1 and FIG. 5.

Comparative Example 2

The compound represented by the following formula (VII) is subjected to treatment for fine particle formation by the method mentioned below.

(VII)

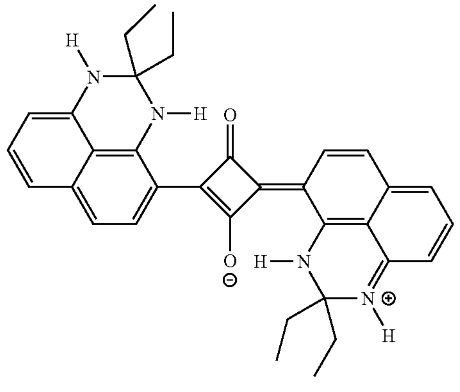

(Reprecipitation Method)

Figure 8:
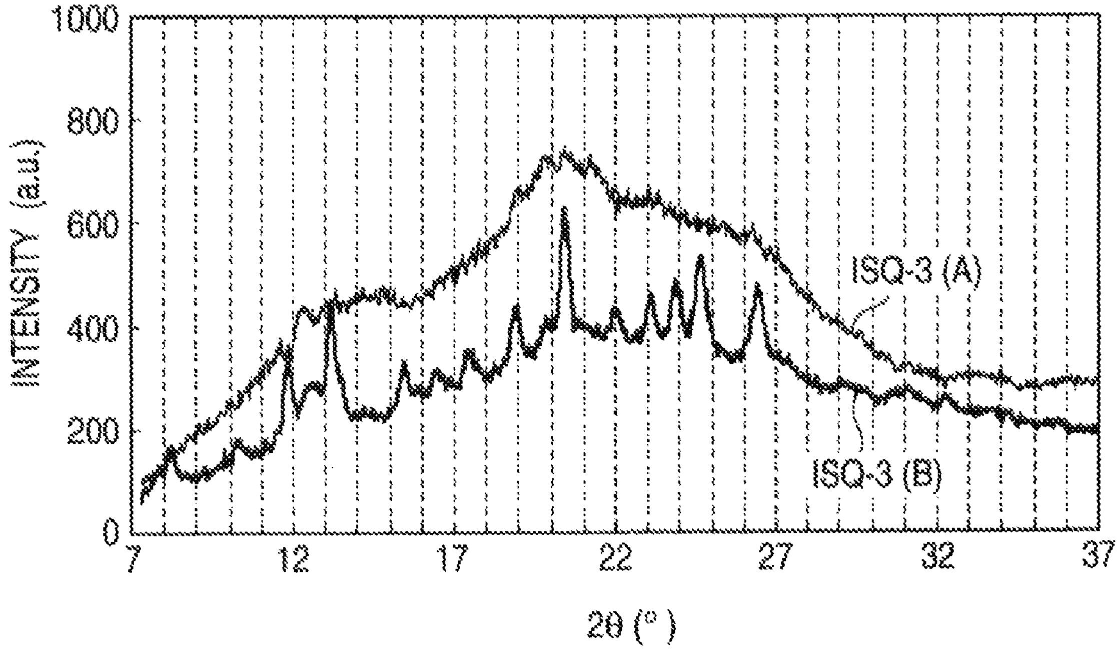
FIG. 8 is a graph showing the powder X-ray diffraction spectra of ISQ-3(A) and ISQ-3(B).

The dye compound represented by the formula (VII) in an amount of 40 mg is dissolved in 30 mL of THF, and the resulting solution is injected at a burst into 2,000 mL of ice-cold distilled water with a microsyringe, thereby reprecipitating the dye compound. After a lapse of several minutes, the mixed solution is restored to room temperature and the precipitate is filtered off by a 50-nm filter, washed with distilled water, and then vacuum-dried. Thus, the reprecipitated dye compound (hereinafter referred to as "ISQ-3(A)") is collected. The particle size of ISQ-3(A) is found to be about 90 nm in terms of median diameter d50. A powder X-ray diffraction spectrum of ISQ-3(A) measured under irradiation with X-ray of λ=1.5405 Å from a Cu target in the same manner as in Example 2 is shown in FIG. 8. In this powder X-ray diffraction spectrum, diffraction peaks coming from crystals are hardly discerned, so it is ascertained that ISQ-3(A) prepared by reprecipitation is amorphous.

Comparative Example 3

(Reprecipitation Method plus Milling Method)

In a ball mill vessel, 40 mg of ISQ-3(A) prepared by the reprecipitation method in Comparative Example 2, 5 mL of hexane and 10 g of agate beads measuring 1 mm in diameter are placed, and subjected to 8-hour milling treatment. Then, water is added to the ball mill vessel, and the resulting mixture is passed through a 50-nm filter to collect the dye compound formed into fine particles (hereinafter referred to as "ISQ-3 (B)"). The particle diameter of ISQ-3(B) is found to be about 90 nm in terms of median diameter d50. A powder X-ray diffraction spectrum of ISQ-3(B) measured under irradiation with X-ray of λ=1.5405 Å from a Cu target in the same manner as in Example 2 is shown in FIG. 8. In this powder X-ray diffraction spectrum, ISQ-3(B) shows diffraction peaks at least at angles 11.9°, 13.1°, 15.4°, 19.0°, 20.4°, 23.0°, 23.9°, 24.6° and 26.4° corresponding to 2θ±0.2° (θ: Bragg angle), which proved that ISQ-3(B) has high crystallinity.

The same colorimetric evaluations and light stability test as in Example 2 are performed on ISQ-3(A) in Comparative Example 2 and ISQ-3(B) in Comparative Example 3. The results obtained are shown in Table 1, FIG. 5 and FIG. 6.

| | Sample | Initial Reflectivity R(%) at 850 nm | ΔE | Readability | Invisibility |
|---|---|---|---|---|---|
| Example 2 | ISQ-10(A) (median diameter d50: 30 nm ϕ) | 14.77 | 8.65 | A | B |
| Example 3 | ISQ-10(B) (median diameter d50: 150 nm ϕ) | 23.66 | 6.7 | B | B |
| Comparative Example 1 | VONPc | 24.76 | 32.4 | B | C |
| Comparative Example 2 | ISQ-3(A) (median diameter d50: 90 nm ϕ, amorphous | 51.73 | 9.02 | C | B |
| Comparative Example 3 | ISQ-3(B) (median diameter d50: 90 nm ϕ, crystalline | 60.72 | 8.9 | C | B |

As shown above, it is apparent that, in the cases of using ISQ-10(A) in Example 2 and ISQ-10(B) in Example 3, improvements in light stability and infrared color-development capability are achieved as the fine particles of the dye hold their invisibility. In particular, ISQ-10(A) in Example 2 and ISQ-10(B) in Example 3 exhibit very high invisibility as compared to VONPc in Comparative Example 1 on condition that their infrared absorption is made equivalent. In addition, ISQ-10(A) in Example 2 and ISQ-10(B) in Example 3 provide improvements in infrared absorbency and light stability while holding invisibility over ISQ-3(A) in Comparative Example 2 and ISQ-3(B) in Comparative Example 3.

What is claimed is:

1. An image-forming material comprising a perimidine-based squarylium dye represented by the following formula (I):

(I)

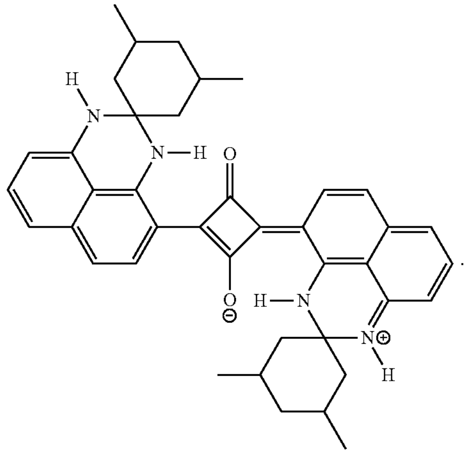

2. The image-forming material as claimed in claim 1, wherein the perimidine-based squarylium dye is present in a state of crystalline particles showing diffraction peaks at least at angles 9.9°, 13.2°, 19.9°, 20.8° and 23.0° corresponding to 2θ±0.2° in powder X-ray diffraction spectrum measured under irradiation with X-ray of 1.5405 Å from a Cu target, wherein θ is Bragg angle.

3. The image-forming material as claimed in claim 1, wherein the perimidine-based squarylium dye is present in a state of crystalline particles having a median diameter d50 in a range of 10 nm to 300 nm.

4. The image-forming material as claimed in claim 1, wherein a content of the perimidine-based squarylium dye is from 0.05% to 3% by weight.

5. The image-forming material as claimed in claim 1, which is an electrophotographic toner, an ink for inkjet printer, or an ink for letterpress, offset, flexographic, gravure or silk-screen printing.

6. The image-forming material as claimed in claim 1, which satisfies conditions given by the following expressions (II) and (III):

$$0 \leqq \Delta E \leqq 16 \quad \text{(II)}$$

$$(100-R) \geqq 75 \quad \text{(III)}$$

wherein ΔE represents a color difference defined by the following expression (IV) in CIE1976L*a*b* color specification system, $$\Delta E=\sqrt{(L_1-L_2)^2+(a_1-a_2)^2+(b_1-b_2)^2} \quad \text{(IV)}$$

wherein $L_1$, $a_1$ and $b_1$ respectively represent an L-value, an a-value and a b-value of a recording medium surface before image formation, and $L_2$, $a_2$ and $b_2$ respectively represent an L-value, an a-value and a b-value of an image area at the time of formation of a fixed image in an adhesion amount of 4 g/$m^2$ on the recording medium surface by using the image-forming material, and R represents a reflectivity-in-percent of the image area when an infrared ray with a wavelength of 850 nm strikes thereon.

* * * * *